United States Patent [19]
Keck

[11] Patent Number: 5,389,068
[45] Date of Patent: Feb. 14, 1995

[54] TAMPON APPLICATOR

[75] Inventor: Laura E. Keck, Decatur, Ga.

[73] Assignee: Kimberly-Clark Corporation, Neenah, Wis.

[21] Appl. No.: 938,963

[22] Filed: Sep. 1, 1992

[51] Int. Cl.$^6$ .............................................. A61F 13/20
[52] U.S. Cl. ...................................... 604/15; 604/11; 604/18
[58] Field of Search ................. 604/1, 11–18, 604/904, 367, 368, 370; 525/60, 326.2, 378, 379; 526/329.5, 320; 428/522; 524/381

[56] References Cited

U.S. PATENT DOCUMENTS

| | | | |
|---|---|---|---|
| 2,518,486 | 8/1950 | Mende | 128/261 |
| 3,546,008 | 12/1970 | Shields et al. | 117/138.8 |
| 3,563,244 | 2/1971 | Asaka | 128/294 |
| 3,724,462 | 4/1973 | Hanke | 128/263 |
| 3,734,874 | 5/1973 | Kibler et al. | 260/29.2 E |
| 3,734,979 | 5/1973 | Koleske et al. | 260/897 R |
| 3,779,993 | 12/1973 | Kibler et al. | 260/75 S |
| 3,859,125 | 1/1975 | Miller et al. | 229/3.5 |
| 3,882,196 | 5/1975 | Hanke | 260/895 |
| 3,882,869 | 5/1975 | Hanke | 128/263 |
| 3,911,917 | 10/1975 | Hanke | 128/263 |
| 3,954,104 | 5/1976 | Kraskin et al. | 128/263 |
| 4,099,976 | 7/1978 | Kraskin et al. | 106/15 R |
| 4,206,101 | 6/1980 | Wysong | 260/23 R |
| 4,233,196 | 11/1980 | Sublett | 260/29.2 N |
| 4,304,901 | 12/1981 | O'Neill et al. | 528/290 |
| 4,317,447 | 3/1982 | Williams | 128/260 |
| 4,372,311 | 2/1983 | Potts | 128/287 |
| 4,503,098 | 3/1985 | Potts | 427/394 |
| 4,618,648 | 10/1986 | Marten | 525/60 |
| 4,618,649 | 10/1986 | Ofstead | 525/60 |
| 4,656,216 | 4/1987 | Muller et al. | 524/381 |
| 4,675,360 | 6/1987 | Marten | 525/60 |
| 4,708,999 | 11/1987 | Marten | 526/320 |
| 4,772,663 | 9/1988 | Marten et al. | 525/60 |
| 4,900,299 | 2/1990 | Webb | 604/11 |
| 4,931,501 | 6/1990 | Lai et al. | 525/61 |
| 5,002,526 | 3/1991 | Herring | 604/11 |
| 5,028,648 | 7/1991 | Famili et al. | 524/317 |

FOREIGN PATENT DOCUMENTS

| | | | |
|---|---|---|---|
| 0057415 | 8/1982 | European Pat. Off. | C08L 67/02 |
| 0291024A2 | 11/1988 | European Pat. Off. | |
| 0435435 | 7/1991 | European Pat. Off. | C08L 67/04 |
| 0438672A1 | 7/1991 | European Pat. Off. | |
| 0481484 | 4/1992 | European Pat. Off. | A61F 13/32 |
| 88/2776 | 4/1988 | South Africa | |
| WO9118036 | 11/1991 | WIPO | C08G 63/688 |

OTHER PUBLICATIONS

"Properties and Potential Applications of Some Novel Water–Dispersible Polyesters" by Barton (Eastman Kodak Co., 1987).

"Polyester Binders for Polyester Nonwovens", *Nonwovens Industry*, May 1979.

*Primary Examiner*—Randall L. Green
*Assistant Examiner*—Elizabeth M. Burke
*Attorney, Agent, or Firm*—Mark L. Davis

[57] ABSTRACT

A tampon applicator is disclosed for inserting tampons into a woman's vagina. The tampon applicator is an elongated, tubular member made from an injection moldable or extrudable material. The tampon applicator comprises a water-dispersible thermoplastic polyester containing an ionic metal salt substituent. The tampon applicator is constructed from a water-dissipatable polymer having carbonyloxy-linking groups in a linear molecular structure. The polymer comprises a reaction product of at least one difunctional dicarboxylic acid, at least one diol, and at least one difunctional sulfomonomer containing at least one metal sulfonate group attached to an aromatic nucleus having the functional group carboxyl. The tampon applicator is water dispersible, compostable, dimensionally stable, and substantially nonsticky when contacted by mucous membranes or other moist human tissue. The injection moldable material of the tampon applicator is compounded from linear thermoplastic polyester blended with a thermoplastic polymer to form a mixture capable of providing the features described above.

18 Claims, 1 Drawing Sheet

TAMPON APPLICATOR

FIELD OF THE INVENTION

This invention relates to tampon applicators and the like. More specifically, this invention relates to means and a method for providing injection molded articles for tampon insertion in feminine care applications.

BACKGROUND OF THE INVENTION

Conventional tampon applicators are constructed to provide a pair of elongated, concentric, telescoping tubes so that the outer tube can carry the tampon's absorbent material, the tampon's "pledget," while the inner tube serves as a plunger for dispensing the pledget.

Currently, commercial tampon applicators are formed from either plastic or paper. Plastic tampon applicators are preferred by many women because of a molded-in grip ring and a petal-shaped forward end which facilitates insertion of the applicator article while retaining and protecting the tampon while in the outer tube. Plastic tampon applicators typically are formed from polyethylene using injection molding.

A convenient place to dispose of a tampon applicator is in a toilet bowl. However, all currently available commercial plastic applicators formed of polyethylene are ill-suited for such disposal. Presently available commercial plastic applicators of polyethylene will flush, but they settle in septic tanks without decomposing. They accumulate on screens in waste-water treatment plants, creating blockages. If the screens do not stop the applicator articles, they can escape into the environment intact, washing up on beaches. Plastic applicators do not always float, so they cannot be skimmed, and they do not settle to the bottom of settling tanks. Consequently, a plastic applicator is needed that is both water dispersible and compostable.

Tampon applicators formed from water-soluble polyvinyl alcohol have been proposed, but such polyvinyl alcohol applicator articles in actual practice have been found to become sticky on contact with moist human tissue. In addition, they tend to be relatively unstable in maintaining their dimensions in humid conditions as found in bathroom environments where tampon applicators are typically stored. These water-soluble polyvinyl alcohol applicator articles can be formed by techniques, such as injection molding, to provide the aforementioned design features of grip ring and front petals, but they can become distorted in humid conditions.

U.S. Pat. No. 3,882,869, issued to Hanke, points out that polyvinyl alcohol articles are unstable in the presence of moisture-laden air, as found in bathroom environments, and the polyvinyl alcohol becomes prematurely sticky when in contact with moist surfaces. The Hanke patent teaches a polyethylene oxide polymer or hydroxypropyl cellulose containing a filler, such as talc.

U.S. Pat. No. 3,724,462, also issued to Hanke, teaches tampon applicators formed of inner and outer tubes made of different water-soluble polymers which are incompatible with one another. This is designed to overcome the problems of tubes fusing or sticking together under high humidity/high temperature conditions.

U.S. Pat. Nos. 3,911,917 and 3,882,196, both issued to Hanke, address a further problem of polyvinyl alcohol in that it suffers from odor, specifically an acetic acid smell.

U.S. Pat. No. 5,002,526, issued to Herring, teaches a tampon applicator prepared from injection moldable or extrudable material of polyvinyl alcohol modified to be self-plasticizing.

The tampon applicators formed from polyvinyl alcohol can provide water dispersibility. However, such applicators, when formulated to provide water dispersibility, are found to become sticky. In addition, the applicators display only limited stability in material and dimensional design for preferred design features, such as a grip ring and front petals.

Consumer demand calls for a quality product in convenience and comfort in feminine care applications. A tampon applicator is currently needed to provide tampon insertion articles or devices which are water dispersible and compostable, yet capable of being fabricated into particular shapes suitable for convenience and comfort in the application. The applicator should have long term stability in humid conditions and should be characterized as substantially nonsticky when contacted by mucous membranes or other moist human tissue.

SUMMARY OF THE INVENTION

Briefly, the present invention provides means and a method for providing a tampon applicator or insertion article for tampons and the like. The present invention includes an injection molded, elongated, tubular member composed of an injection moldable or extrudable material comprising water-dispersible thermoplastic polyester containing ionic metal salt substituent. In one aspect, the present invention includes an article and a method for providing a tampon applicator of an injection molded, tubular member composed of a linear, water-dissipatable polymer having carbonyloxy-linking groups in the linear molecular structure. The polymer can include the reaction product of at least one difunctional dicarboxylic acid, at least one diol, and at least one difunctional sulfomonomer containing at least one metal sulfonate group attached to an aromatic nucleus having the functional group carboxyl. In another aspect, the present invention includes an article and a method for providing a tampon applicator which is water dispersible, compostable, stable, and characterized as substantially nonsticky when contacted by mucous membranes or other moist, human tissue. Furthermore, the injection moldable material of the article, and the method of forming the article, is compounded from linear, thermoplastic polyester blended with a thermoplastic polymer to form a polymer mixture capable of providing the features of the article and method of the present invention.

The general object of the present invention is to provide a tampon applicator. A more specific object of this invention is to provide means and a method for providing articles for tampon insertion, which articles are water dispersible, such that disposal through conventional toilet facilities is feasible.

It is another object of the present invention to provide means and a method for providing articles for tampon insertion, which articles are compostable, such that disposal through conventional toilet facilities is feasible.

It is another object of the present invention to provide means and a method for providing injection molded tampon insertion articles or devices of a shape and design suitable for convenience and comfort in feminine care applications.

It is a further object of the present invention to provide means and a method for producing insertion articles or devices in particular shapes and designs which are stable in dimension and material for long term storage periods in high humidity conditions as experienced in bathroom environments.

It is yet another object of the present invention to provide efficient means and a method for producing articles for tampon insertion, which articles are substantially nonsticky when contacted by mucous membranes or other moist human tissue.

These, and other objects of the present invention, will become apparent from the detailed description which follows.

DETAILED DESCRIPTION OF THE PREFERRED EMBODIMENTS

Figure 1:
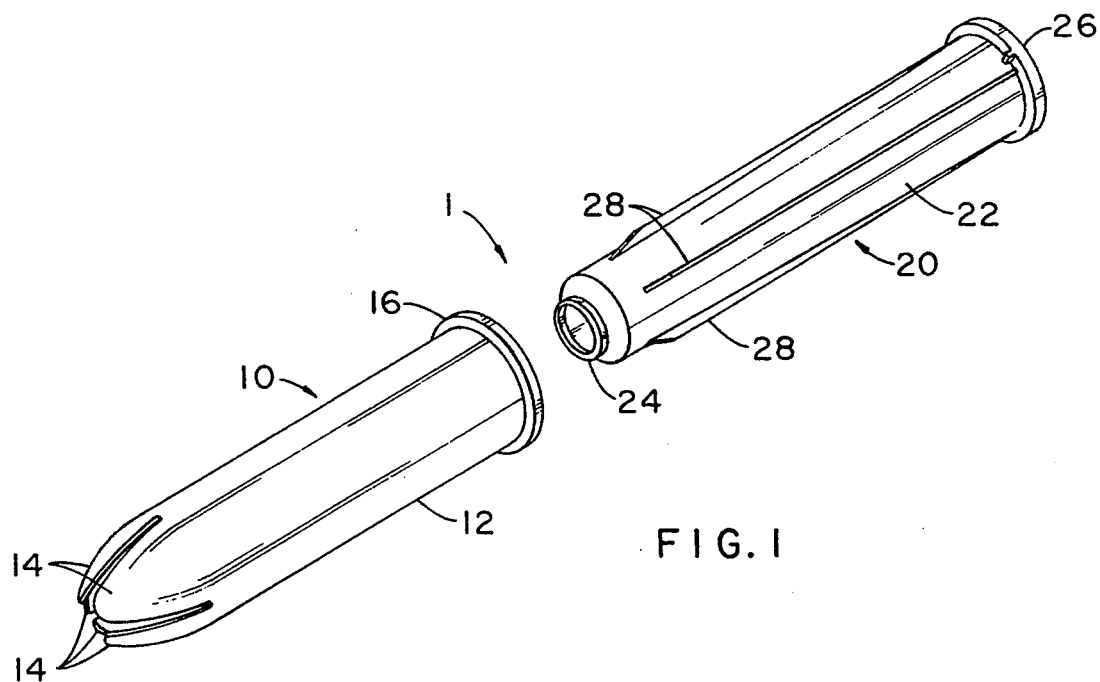
FIG. 1 presents an oblique view of a tampon applicator in accordance with the present invention.

Referring to FIG. 1, a tampon applicator 1 includes an outer tubular member 10 and a plunger 20. The outer tube 10 preferably is fabricated to include a one-piece main cylindrical body 12 extending into five flexible petal tips 14 disposed on the front end of the outer tube 10. A grip ring 16 is formed on the opposite end of the outer tube 10. The tampon applicator 1 further includes the plunger 20 with a plunger body 22 adapted to serve as an inner tubular member. The plunger 20 is designed to urge a pledget (not shown), housed in the hollow cylindrical body 12 of the outer tubular member 10, through the open petal tips 14 and, further, to insert the pledget into a woman's vagina. Insertion end 24 of the plunger 20 pushes against the tampon so as to expel it from the outer tube 10. The plunger 20 has structural guide ridges 28 molded into the tubular wall 22 to provide strength and to reduce the wall dimension to form a thin wall plunger.

Tampon applicator 1 is designed to insert a tampon into a woman's vagina. The outer tube 10 and the plunger 20 provide a pair of elongated, concentric, telescoping tubes, including a one-piece molded outer tube 10 and a one-piece molded inner tube 20. The outer tube 10 includes a one-piece, elongated cylindrical body 12. Petals 14 are formed on the front end of the cylindrical body 12, and a grip ring 16 is formed on the other end. The one-piece plunger 20 also has a grip ring 26 which is sized to contact the grip ring 16. This contact will occur when the plunger 20 has expelled the tampon pledget from the outer tube 10. The grip ring 26 limits the travel of the plunger 20 into the outer tube 10, while the grip ring 16 facilitates withdrawal of the tampon applicator 1 from the woman's vagina after insertion of the pledget.

Figure 2:
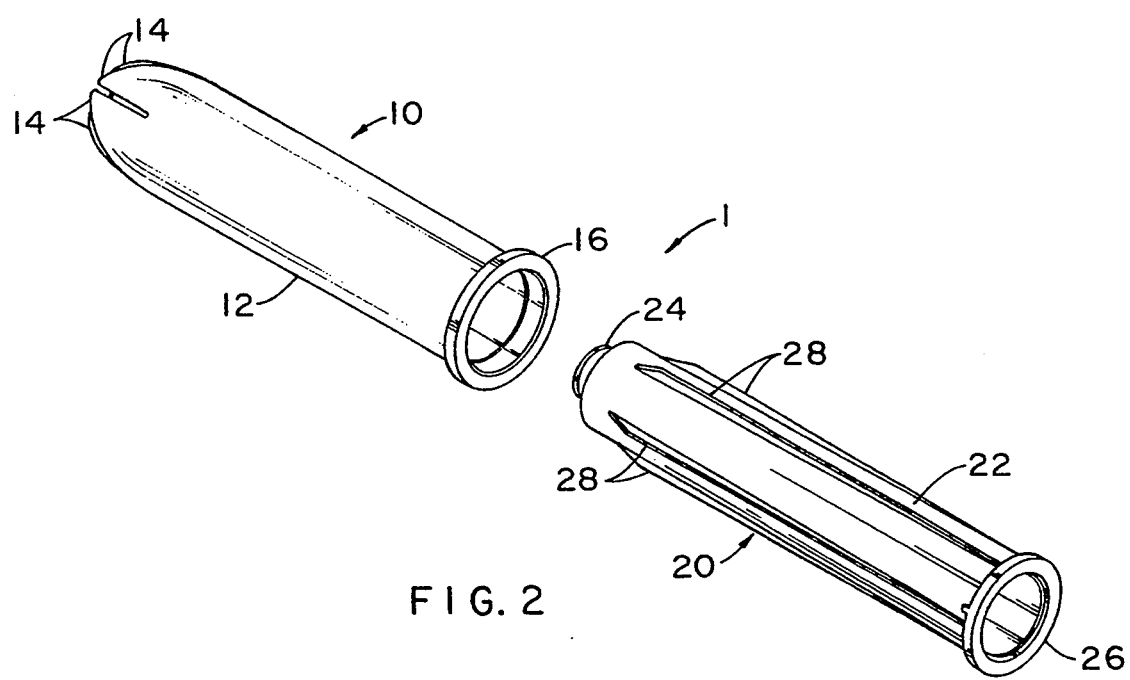
FIG. 2 depicts an oblique view of a tampon applicator from perspective reverse from that shown in FIG. 1.

FIG. 2 shows the tampon applicator 1 from a reverse angle. The outer tube 10 is a hollow member having an elongated, tubular body 12 disposed to accept the plunger 20.

The one-piece, concentric tubular members 10 and 20 are preferably formed by injection molding. The tubular members 10 and 20 can be composed of an injection moldable or extrudable material. The material comprises water-dispersible, thermoplastic polyester containing ionic metal salt substituent.

In one aspect, the injection molded tubular members 10 and 20 can be composed of a linear, water-dissipatable polymer having carbonyloxy-linking groups in the linear, molecular structure. The polymer can comprise the reaction product of at least one difunctional dicarboxylic acid, at least one diol, and at least one difunctional sulfomonomer containing at least one metal sulfonate group attached to an aromatic nucleus having the functional group carboxyl.

The polymer can be represented simply by formula (1).

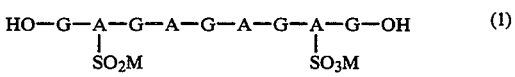

(1)

The simple representation of formula (1) is not intended to describe a polymer limited to the number of constituents shown here. Rather, the number of repeating monomer constituents will be described by reference to molecular weight. Such a polymer is available from Eastman Chemical Products, Inc., Kingsport, Tenn., under the trademark Eastman AQ® polymer. The Eastman polymers are described and claimed in U.S. Pat. Nos. 3,546,008, 3,734,874, 3,779,993, 4,233,196, and 4,304,901 and are incorporated by reference and made a part hereof.

This water-dispersible thermoplastic polyester has a structure containing primary hydroxy groups (—OH) at most of the end groups. The water-dispersible thermoplastic polyester includes structure containing sulfonate ion metal salt substituent. Preferably, the sulfonate includes alkali metal sulfonyl salt substituent. In one aspect, the alkali metal sulfonyl salt comprises sodium sulfonyl salt.

It has been found that the preferred thermoplastic polyester polymer, as used in the article and method of the present invention, is the Eastman AQ® 29S thermoplastic polyester. The Eastman AQ® 29S thermoplastic polyester is dispersible in water, yet has a non-tacky surface. However, because the glass transition temperature of this polymer is about 29° C., the polymer is brittle at room temperature. The polymer is not known to have been injection molded previously.

The preferred thermoplastic polyester polymer should be an alkali metal sulfonate, as represented by the simplistic schematic shown in formula (2).

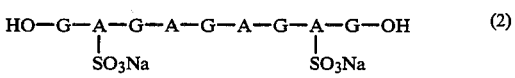

(2)

The simple representation of formula (2) is not intended to describe a polymer limited to the number of constituents shown here. Rather, the number of repeating monomer units will be described by reference to molecular weight. Molecular weight of the polymer represented in the equation preferably is in the range of about 13,000 to about 19,000 daltons.

The linear thermoplastic polyester, as used in the article and method of the present invention, can be specified with more particularity. Preferably, the molecular weight of the polymer can range from about 14,000 to about 18,000 daltons and, more preferably, from about 15,000 to about 17,000 daltons.

In one embodiment of the sulfomonomer substituent, sodiosulfo groups (—$SO_3Na$) are responsible primarily for the water dispersibility of the thermoplastic polyesters. The terms dispersible, dispersibility, dissipatable, or dissipatability will be used to mean dispersible in water or aqueous solution (preferably of at least 98 weight percent of water).

The thermoplastic polyesters are noncrystalline and contain a hydrophobic moiety and a hydrophilic moiety. For example, in one representation of the hydrophobic and hydrophilic moieties, the polyester composition can be prepared from isophthalic acid (hydrophobic), the sodium salt of 5-sulfo-isophthalic acid (hydrophilic) and diethylene glycol (hydrophilic). When added to water, this composition forms a dispersion having a viscosity higher than that of water, but lower than that of a solution with the polymer completely dissolved. As the temperature is raised from 25° C. to 90° C., the polymer displays no appreciable increase in dispersion or solution viscosity. The polymer composition thereby acts as partially soluble in water and partially insoluble. Such behavior is consistent with its hydrophobic-hydrophilic composition.

As used in the article and method of the present invention, the hydrophobic and hydrophilic portions of the molecule of the polyester can be increased or decreased to provide the desired water dispersibility while maintaining a substantially nontacky surface condition. Accordingly, water dispersibility can be achieved while maintaining a substantially nontacky surface condition when coming in contact with mucous membranes, or other moist human tissue, as in feminine care applications.

Moreover, water dispersibility is achieved while maintaining storage stability in humid environments, as found in a bathroom environment, for example, to retain dimensional and material integrity during long term storage of the tampon applicator.

In a preferred embodiment, in the means and method for providing the tampon applicator, the thermoplastic polyester includes a linear chain polymer containing about 5 to about 8 sodiosulfo monomers per molecule. The difunctional sulfomonomer includes from about 6 mole percent to about 25 mole percent out of a total of about 200 mole percent of difunctional dicarboxylic acid, difunctional glycol, and difunctional sulfomonomer components of the polyester.

The material, from which the tampon applicator is formed, can be a mixture compounded from linear thermoplastic polyester blended with a polymer. Suitable polymers that work well are polycaprolactone or polyethylene.

A preferred composition for the tampon applicator includes an injection moldable material of a blend of at least about 70 weight percent of the linear, water-dissipatable thermoplastic polyester and a suitable blended polymer. More preferably, the composition for the tampon applicator includes an injection moldable material formed of a blend of at least about 74 weight percent of the linear, water-dissipatable thermoplastic polyester and a suitable blended polymer, for example, a suitable polycaprolactone.

The thermoplastic polyester can have carbonyloxy-linking groups in the linear molecular structure and have substantially equimolar proportions of acid equivalents to hydroxy equivalents. The polyester can further comprise the reaction product of at least one difunctional dicarboxylic acid, at least one difunctional sulfomonomer and at least one difunctional glycol. The sulfomonomer should be in an amount of a specified weight percent of total acid and hydroxyl equivalents and contain at least one metal sulfonate group attached to an aromatic nucleus having at least one carboxyl functional group. The polyester can further be characterized as having a specified molecular weight greater than about 15,000 and less than about 17,000 daltons. The specified weight percent of difunctional sulfomonomer includes from about 6 mole percent to about 25 mole percent out of a total of about 200 mole percent of difunctional dicarboxylic acid, difunctional glycol, and difunctional sulfomonomer components of the polyester.

A polymer blend, in accordance with the present invention, can be prepared using at least about 70 weight percent of Eastman LB-100 AQ® 29S polyester which contains a small amount of a sodium aluminum silicate. The Eastman polyester LB-100 is a "low-block" formulation of AQ® 29S, and the sodium aluminum silicate prevents the polymer pellets from agglomerating when warm or bridging in the hopper of injection molding equipment. The water dispersibility of the polymer blend is compromised when prepared using amounts less than about 70 weight percent.

Injection molding of the thermoplastic material can be performed using conventional injection molding equipment using well-known procedures. Specific processing conditions will vary with different equipment and the type of molds or dies used. For a general description of injection molding, refer to "Injection Molding," by Rubin in *Encyclopedia of Polymer Science and Engineering*, (Wiley and Sons, 1987), Volume 8, pages 102–138.

Tampon applicator tubes molded from 100% Eastman AQ® 29S polyester were found to be brittle and stiff at room temperature and were nonresilient, losing the intended shape by flattening and shrinking.

Tampon applicator tubes injection molded from material compounded from Eastman AQ® 29S and polycaprolactone or polyethylene, or mixtures thereof, provide water-dispersible, resilient, flexible, and strong tampon applicators.

Polycaprolactone polymers used to form the tampon applicator are commercially available from Union Carbide Corporation under the description Tone P-767 and P-303 polycaprolactone polymers. Tone P-767 polycaprolactone has a molecular weight of about 43,000 daltons. Tone P-303 is an A-B-A block polymer of Tone P-767 polycaprolactone and polyethylene oxide. Tone P-303 polycaprolactone has a molecular weight of about 30,000 to about 35,000 daltons.

A polyethylene polymer used to form the tampon applicator is commercially available from Dow Chemical, Midland, Mich., under the description Dowlex 2503 linear low density polyethylene.

A slip agent, suitable for use in the tampon applicator, is commercially available from Eastman Chemical Products, Inc. This product is sold as Epolene C-10 wax, a highly branched polyethylene wax having a molecular weight of about 8,000 daltons.

An optical brightener, suitable for use in the tampon applicator, is commercially available from Eastman Chemical Products, Inc. This product is sold as Eastobrite OB-1, which is 2,2'-(1,2-ethenediyldi-4,1-phenylene)bisbenzoxazole.

The tampon applicator compounded from linear thermoplastic polyester and blended with a polymer is water dispersible and compostable. It is capable of being fabricated into more particular shapes suitable for the application. It is also stable over the long term in humid conditions and is substantially nonsticky when contacted by mucous membranes or other moist human tissue.

The following examples illustrate the practice of the invention in more detail, using different polymer blends. Examples 1-4 represent polymer blends which were unacceptable, while examples 5-7 represent polymer blends which were acceptable.

EXAMPLE I

A thermoplastic polymer, Eastman AQ® 29S polyester, was injection molded into a tampon applicator shape as depicted in FIG. 1. The thermoplastic polyester was molded in a Battenfeld Model 1600 injection molding machine using a 45 mm diameter screw with the following conditions. For temperature control, the barrel of the injection molding machine is divided into 20 zones, each with its own thermocouple and temperature-control instrument.

| Temperatures: | |
| --- | --- |
| Nozzle | 465° F. (241° C.) |
| Zone 2 (front) | 464° F. (240° C.) |
| Zone 3 (center) | 437° F. (225° C.) |
| Zone 4 (center) | 431° F. (222° C.) |
| Zone 5 (rear) | 410° F. (210° C.) |
| Mold | 85° F. (29° C.) |
| Injection pressure | 1406 psi |
| Holding pressure | 900 psi |
| Hold time | 1.5 seconds |
| Injection speed | 6.1 inches per second |
| Cool time | 40 seconds |

The injection molded tampon applicators, molded from 100% Eastman AQ® 29S polyester pellets, were observed to exhibit unacceptable shrinkage and nonresiliency, as measured by comparison to polyethylene.

EXAMPLE II

A polymer blend was prepared from a mixture of Eastman AQ® 29S polyester pellets, calcium carbonate ($CaCO_3$), and additives of 1% slip agent, plasticizer, and 3% titanium dioxide. The compositions are listed in Table I as components based on percent by weight.

TABLE I

| | C1 | C2 |
| --- | --- | --- |
| Eastman AQ® 29S | 83 | 74 |
| $CaCO_3$ | 9 | 20 |
| Plasticizer | 4 | 2 |
| $TiO_2$ | 3 | 3 |
| Slip Agent | 1 | 1 |

The blended components were compounded using a single-screw extruder with ¾ inch screw diameter manufactured by C. W. Brabender Instrument, Inc. at 60 rpm, at temperatures ranging from about 125° C. at the feed section to about 170° C. at the die tip.

The C1 blend was then molded in a Battenfeld Model 1600 injection molding machine using a 45 mm diameter screw with the following conditions:

| Temperatures: | |
| --- | --- |
| Nozzle | 465° F. (241° C.) |
| Zone 2 (front) | 464° F. (240° C.) |
| Zone 3 (center) | 437° F. (225° C.) |
| Zone 4 (center) | 431° F. (222° C.) |
| Zone 5 (rear) | 410° F. (210° C.) |
| Mold | 85° F. (29° C.) |
| Injection pressure | 1406 psi |
| Holding pressure | 900 psi |
| Hold time | 1.5 seconds |
| Injection speed | 6.1 inches per second |
| Cool time | 40 seconds |

The injection molded tampon applicators molded from the material of C1 were observed to exhibit unacceptable shrinkage and nonresiliency, as measured by comparison to polyethylene. The material of C2 was observed to form unacceptable brittle strands and was not molded.

EXAMPLE III

A polymer blend was prepared from a mixture of Eastman AQ® 29S polyester pellets, Tone P-767 polycaprolactone, and about 1% titanium dioxide. The compositions are listed in Table II as components based on percent by weight.

TABLE II

| | PCL1 | PCL2 |
| --- | --- | --- |
| Eastman AQ® 29S | 74 | 64 |
| PCL 700/767 | 25 | 35 |
| $TiO_2$ | 1 | 1 |

The blended components were compounded using a single-screw extruder with ¾ inch screw diameter manufactured by C. W. Brabender Instruments, Inc., at 21 rpm, at temperatures ranging from about 110° C. at the feed section to about 177° C. at the die tip.

The blend was then molded in a Battenfeld Model 1600 injection molding machine using a 45 mm diameter screw with the following conditions:

| Temperatures: | |
| --- | --- |
| Nozzle | 320° F. (160° C.) |
| Zone 2 (front) | 310° F. (154° C.) |
| Zone 3 (center) | 290° F. (143° C.) |
| Zone 4 (center) | 280° F. (138° C.) |
| Zone 5 (rear) | 250° F. (121° C.) |
| Mold | 80° F. (27° C.) |
| Injection pressure | 855 psi |
| Holding pressure | 425 psi |
| Hold time | 1 second |
| Injection speed | 6.2 inches per second |
| Cool time | 90 seconds |

The injection molded tampon applicators molded from the material of PCL1 were observed to exhibit unacceptable nonresiliency, as measured by comparison to polyethylene. The material of PCL2 was observed to exhibit unacceptable nondispersibility.

EXAMPLE IV

A polymer blend was prepared from a mixture of Eastman LB-100 AQ® 29S polyester pellets, Tone P-303 polycaprolactone, Tone P-767 polycaprolactone, Dowlex linear low density polyethylene, titanium dioxide, and plasticizer. The compositions are listed in Table III as components based on percent by weight.

TABLE III

| | PCL3 | PCL4 |
| --- | --- | --- |
| Eastman AQ® 29S | 70 | 75 |

TABLE III-continued

|  | PCL3 | PCL4 |
|---|---|---|
| PCL 700/767 | 10 | 15 |
| PCL 303 | 9 |  |
| LLDPE | 10 | 5 |
| Plasticizer |  | 4 |
| TiO$_2$ | 1 | 1 |

The blended components were compounded using a single-screw extruder with ¾ inch screw diameter manufactured by C. W. Brabender Instrument, Inc. at 31 rpm, at temperatures ranging from about 110° C. at the feed section to about 140° C. at the die tip.

The PCL4 blended components were compounded using a twin-screw extruder with 30 mm screw diameter manufactured by Werner and Pfleiderer, at 202 rpm, at temperatures ranging from about 95° C. at the feed section to about 126° C. at the die tip. Strands were cooled (quenched) with blown air over a 24 ft. conveyor.

The blend was then molded in a Battenfeld Model 1600 injection molding machine using a 45 mm diameter screw with the following conditions:

|  | PCL3 | PCL4 |
|---|---|---|
| Nozzle | 330° F. (166° C.) | 360° F. (182° C.) |
| Zone 2 (front) | 300° F. (149° C.) | 355° F. (179° C.) |
| Zone 3 (center) | 260° F. (127° C.) | 345° F. (174° C.) |
| Zone 4 (center) | 210° F. (99° C.) | 322° F. (161° C.) |
| Zone 5 (rear) | 160° F. (71° C.) | 300° F. (149° C.) |
| Injection pressure | 330 psi | 600 psi |
| Holding pressure | 145 psi | 300 psi |
| Hold time | 0.3 sec. | 1.2 sec. |
| Injection speed | 6.0 in./sec. | 6.1 in./sec. |
| Cool time | 40 sec. | 40 sec. |

The injection molded tampon applicators molded from the material of PCL3 were observed to exhibit unacceptable nondispersibility. The material of PCL4 was observed to exhibit unacceptable stiffness, as measured by comparison to polyethylene.

EXAMPLE V

A polymer blend was prepared from a mixture of about 74% by weight of Eastman LB-100 AQ® 29S polyester pellets, about 14% by weight Tone P-303 polycaprolactone, about 4% Tone P-767 polycaprolactone, about 5% Dowlex linear low density polyethylene, about 2% Epolene C-10 polyethylene wax, 1% titanium dioxide, and 250 ppm Eastobrite OB-1 optical brightener. The blended components were compounded using a twin-screw extruder with 30 mm screw diameter manufactured by Werner and Pfleiderer, at 202 rpm, at temperatures ranging from about 95° C. at the feed section to about 126° C. at the die tip. Strands were cooled (quenched) with blown air over a 24 ft. conveyor. The blend was then molded in a Battenfeld Model 1600 injection molding machine using a 45 mm diameter screw with the following conditions:

| Temperatures: |  |
|---|---|
| Nozzle | 360° F. (182° C.) |
| Zone 2 (front) | 355° F. (179° C.) |
| Zone 3 (center) | 350° F. (177° C.) |
| Zone 4 (center) | 332° F. (167° C.) |
| Zone 5 (rear) | 300° F. (149° C.) |
| Mold | 90° F. (32° C.) |
| Injection pressure | 333 psi |
| Holding pressure | 150 psi |
| Hold time | 1.2 seconds |
| Injection speed | 3.6 inches per second |
| Cool time | 60 seconds |

The injection molded tampon applicator tubes were observed to have the following characteristics: proper color (white), flexibility and resilience approximate to linear low density polyethylene, and nontacky surface. The tampon applicator tubes dispersed in tap water stirred at about 80 rpm at room temperature (21° C.) with in two (2) hours.

Tampon applicators prepared from the polymer blend described in Example I were tested for flushability in two types of toilets. A first type of toilet was a common household toilet having 4.5 gallon flush volume. The second type of toilet was a Kohler watersaver toilet with 1.5 gallon flush volume. A combination of a tampon applicator consisting of an outer tube 10 and a plunger 20, a 3.4 gram pledget (Kotex® Security® tampon pledget, size "Super"), and eighteen standard toilet paper squares were flushed in each toilet. The results showed all of the items cleared the toilet bowls on the first flush.

EXAMPLE VI

A polymer blend was prepared from a mixture of about 75% by weight of Eastman LB-100 AQ® 29S polyester pellets, about 15% by weight Tone P-303 polycaprolactone, about 5% Tone P-767 polycaprolactone, about 4% Epolene C-10 polyethylene wax, 1% titanium dioxide, and 250 ppm Eastobrite OB-1 optical brightener. The blended components were compounded using a twin-screw extruder with 30 mm screw diameter, at 202 rpm, at temperatures ranging from about 95° C. at the feed section to about 126° C. at the die tip. The blend was then molded in the Battenfeld Model 1600 injection molding machine using a 45 mm diameter screw with essentially the same conditions employed in Example I.

The injection molded tampon applicator tubes were observed to have the following characteristics: proper color (white), flexibility and resilience approximate to linear low density polyethylene, and nontacky surface. The tampon applicator tubes dispersed in tap water stirred at about 80 rpm at room temperature (21° C.) within two (2) hours.

Tampon applicators prepared from the polymer blend described in Example VI were tested for flushability in the two types of toilets described in Example V. A combination of a tampon applicator consisting of an outer tube 10 and a plunger 20, one 3.4 gram pledget (Kotex® Security® tampon pledget, size "Super"), and eighteen standard toilet paper squares were flushed in each toilet. The results showed all of the items cleared the toilet bowl on the first flush.

EXAMPLE VII

A polymer blend was prepared from a mixture of about 75% by weight of Eastman LB-100 AQ® 29S polyester pellets, about 17% by weight Tone P-303 polycaprolactone, about 5% Tone P-767 polycaprolactone, about 2% Epolene C-10 polyethylene wax, 1% titanium dioxide, and 250 ppm Eastobrite OB-1 optical brightener. The blended components were compounded using a twin-screw extruder with 30 mm screw diameter, at 202 rpm, at temperatures ranging from about 95° C. at the feed section to about 126° C. at the die tip. The blend was then molded in the Battenfeld Model 1600 injection molding machine with 45 mm diameter screw using essentially the same conditions employed in Examples I and II.

The injection molded tampon applicator tubes were observed to have the following characteristics: proper color (white), flexibility and resilience approximate to linear low density polyethylene, and nontacky surface. The tampon applicator tubes dispersed in tap water stirred at about 80 rpm at room temperature (21° C.) within two (2) hours.

Tampon applicators prepared from the polymer blend described in Example VII were tested for flushability in the two types of toilets described in Example V. A combination of tampon applicator, consisting of an outer tube 10 and a plunger 20, a 3.4 gram pledget (Kotex® Security® tampon pledget of Super size), and eighteen standard toilet paper squares were flushed in each toilet. The results showed all of the items cleared the toilet bowl on the first flush.

The tampon applicator and method of forming the applicator are not limited to the descriptions of specific embodiments hereinabove, but rather the article and method of the present invention should be viewed in terms of the claims which follow and equivalents thereof.

I claim:

1. A tampon applicator comprising a tubular member composed of a water-dissipatable polymer having a linear molecular structure and having carbonyloxy-linking groups in said linear molecular structure, said polymer comprising a reaction product of at least one difunctional dicarboxylic acid, at least one diol, and at least one difunctional sulfomonomer containing at least one metal sulfonate group attached to an aromatic nucleus having at least one carboxyl functional group; and a second polymer in a blended mixture wherein at least 70 weight percent of said mixture is said water-dissipatable polymer.

2. The tampon applicator as set forth in claim 1 wherein said first polymer further comprises substantially equimolar proportions of acid equivalents to hydroxy equivalents.

3. The tampon applicator as set forth in claim 2 wherein said diol comprises difunctional glycol.

4. The tampon applicator as set 'forth in claim 1 wherein said second polymer is selected from the group consisting of polycaprolactone, polyethylene and mixtures thereof.

5. The tampon applicator as set forth in claim 4 including a one-piece molded insertion article having an elongated, cylindrical body terminating in petals at a front end and having a grip ring at an opposite end.

6. The tampon applicator as set forth in claim 5 wherein said difunctional sulfomonomer comprises from about 6 mole percent to about 25 mole percent out of a total of about 200 mole percent of difunctional dicarboxylic acid, difunctional glycol, and difunctional sulfomonomer components of the polymer.

7. The tampon applicator as set forth in claim 6 wherein said water-dissipatable polymer has a molecular weight in the range of about 13,000 daltons to about 19,000 daltons.

8. The tampon applicator of claim 4 wherein said polyethylene is linear low density polyethylene.

9. The tampon applicator of claim 4 wherein said polycaprolactone has a molecular weight of from about 30,000 to about 43,000 daltons.

10. A tampon applicator comprising an elongated tubular member composed of a material comprising a water-dispersible thermoplastic polyester containing ionic metal salt substituent and a thermoplastic polymer in a blended mixture wherein at least 70 weight percent of said mixture is said water-dispersible polyester, and an insertion device for expelling a tampon from said tubular member.

11. The tampon applicator as set forth in claim 10 wherein said thermoplastic polyester contains sulfonate groups in said ionic metal salt substituent.

12. The tampon applicator as set forth in claim 9 wherein said thermoplastic polymer comprises polycaprolactone having a molecular weight of from about 30,000 daltons to about 43,000 daltons.

13. The tampon applicator as set forth in claim 12 wherein said ionic metal salt substituent comprises an alkali metal sulfonyl salt.

14. The tampon applicator as set forth in claim 13 wherein said alkali metal sulfonyl salt comprises sodium sulfonyl salt.

15. The tampon applicator as set forth in claim 14 wherein said thermoplastic polyester comprises a linear chain polymer containing about 5 to about 8 sodiosulfo monomers per molecule.

16. The tampon applicator as set forth in claim 15 wherein said material has a specified molecular weight greater than about 14,000 and less than about 18,000 daltons.

17. The tampon applicator as set forth in claim 16 wherein said thermoplastic polyester comprises a condensation product of 5-(sodiosulfo) isophthalic acid and diethylene glycol.

18. A tampon applicator comprising an injected molded insertion article for feminine care applications, said insertion article having an outer tubular member and an inner elongated, telescoping tubular member, said outer tube terminating in petals at a front end and having a grip ring at an opposite end, said inner tube having a front end and a grip ring on an opposite end, said insertion article being composed of an injection moldable material comprising a blend having at least 74 weight percent of a water-dissipatable thermoplastic polyester having a linear molecular structure and a polymer selected from the group consisting of polycaprolactone and polyethylene, said thermoplastic polyester having carbonyloxy-linking groups in said molecular structure and having substantially equimolar proportions of acid equivalents to hydroxy equivalents, wherein said thermoplastic polyester further comprises a reaction product of at least one difunctional dicarboxylic acid, at least one difunctional sulfomonomer in an amount of from about 6 mole percent to about 25 mole percent out out of a total of about 200 mole percent of total acid and hydroxyl equivalents and containing at least one metal sulfonate group attached to an aromatic nucleus having carboxyl functionality, and at least one difunctional glycol, said thermoplastic polyester further having a molecular weight greater than about 15,000 and less than about 17,000 daltons.

* * * * *